(12) United States Patent
Kanner et al.

(10) Patent No.: US 8,191,457 B2
(45) Date of Patent: Jun. 5, 2012

(54) ACTUATING MECHANISM FOR FLUID DISPLACEMENT AND PRESSURIZING DEVICE

(75) Inventors: Rowland W. Kanner, Guntersville, AL (US); Richard M. Davis, Huntsville, AL (US)

(73) Assignee: Atrion Medical Products, Inc., Arab, AL (US)

( * ) Notice: Subject to any disclaimer, the term of this patent is extended or adjusted under 35 U.S.C. 154(b) by 768 days.

(21) Appl. No.: 12/341,678

(22) Filed: Dec. 22, 2008

(65) Prior Publication Data

US 2010/0116360 A1    May 13, 2010

Related U.S. Application Data

(60) Provisional application No. 61/114,192, filed on Nov. 13, 2008.

(51) Int. Cl.
*A61B 17/70* (2006.01)
*F16H 25/20* (2006.01)

(52) U.S. Cl. ..................... 92/15; 604/100.02
(58) Field of Classification Search .. 92/15; 604/100.02
See application file for complete search history.

(56) References Cited

U.S. PATENT DOCUMENTS

| 4,838,864 A * | 6/1989 | Peterson ............... 604/100.02 |
| 5,168,757 A | 12/1992 | Rabenau et al. |
| 5,246,011 A | 9/1993 | Caillouette |
| 5,713,242 A | 2/1998 | Kanner et al. |
| 6,190,354 B1 | 2/2001 | Sell et al. |
| 6,796,959 B2 | 9/2004 | Davis et al. |
| 6,938,319 B2 | 9/2005 | Davis et al. |
| 2004/0122361 A1 | 6/2004 | Hart et al. |
| 2004/0260238 A1 | 12/2004 | Call |

FOREIGN PATENT DOCUMENTS

| KR | 10-0905486 | 7/2009 |
| KR | 10-2009-0097664 | 9/2009 |

OTHER PUBLICATIONS

European Search Report and Opinion which issued in connection with corresponding European Patent Application No. 09075410 on Feb. 16, 2010.

* cited by examiner

*Primary Examiner* — Thomas E Lazo
(74) *Attorney, Agent, or Firm* — Clark Hill PLC (57) ABSTRACT

A fluid displacement device, particularly for use of the device to pressurize balloon catheters, or the like. The device includes a plunger which is displaceable through a housing, and an actuating mechanism which engages the plunger. The actuating mechanism includes a nut member that is biased into engagement with a threaded portion of the plunger. The device has a press-to-release feature wherein the plunger is instantly releaseable by simply depressing a toggle lever of the nut member to overcome a restorative spring force. Subsequently, the plunger can be translated using macro movements (i.e., by pushing or pulling the plunger).

19 Claims, 10 Drawing Sheets

ACTUATING MECHANISM FOR FLUID DISPLACEMENT AND PRESSURIZING DEVICE

RELATED APPLICATION

Priority Claim

This application claims the benefit of U.S. Provisional Application Ser. No. 61/114,192, filed Nov. 13, 2008, which is hereby incorporated herein by reference in its entirety.

BACKGROUND

This invention relates to fluid pressurizing devices for balloon catheters or the like, and more particularly relates to an improved device for actuating a screw plunger and monitoring the resulting fluid pressurization.

Fluid pressurization devices adapted for selectively applying and relieving a measured pressure on a closed volume of fluid have been developed for use in inflation and deflation of a balloon catheter used in angioplasty balloon procedures interiorly of blood vessels, or other types of balloon catheterization procedures. For example, U.S. Pat. No. 4,838,864 discloses a syringe device which inflates and deflates a catheterized balloon. The device uses a manually-operated screw plunger to achieve or maintain specific balloon pressure, and the pressure is monitored using an associated pressure gauge. Improved syringing and pressurization control is also described in U.S. Pat. Nos. 5,168,757; 5,713,242; and 6,796,959, all three of which are owned by the assignee of the present invention and are hereby incorporated herein in their entirety by reference. These patents disclose quick release mechanisms which enable rapid advancement of a plunger and alternatively allow threaded engagement with the screw plunger to achieve precise control during final pressurization of a balloon catheter.

Figure 1:
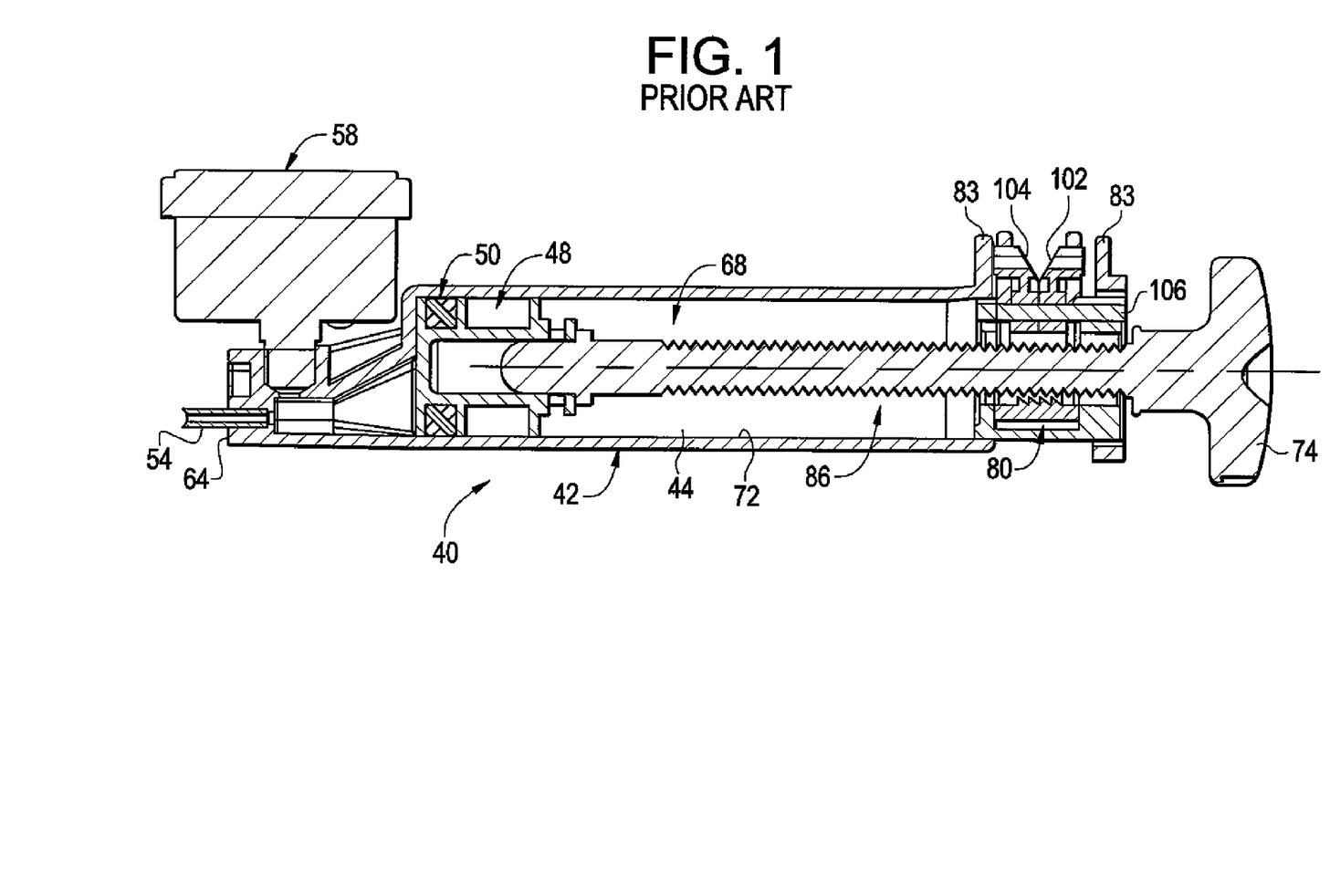
FIG. 1 is a cross-sectional view of a prior art fluid displacement device, specifically that which is disclosed in U.S. Pat. No. 6,796,959.

A cross-sectional view of the device which is disclosed in U.S. Pat. No. 6,796,959 is shown generally in FIG. 1 herein (FIG. 1 herein corresponds to FIG. 4 of the '959 patent). As shown, the device 40 provides that a piston 48 is engaged with a plunger 68 inside a fluid displacement chamber 44 that is provided in a cylindrical syringe body or housing 42. A pressure gauge assembly 58 is threadably engaged with the housing 42, and the end 64 of the housing 42 is configured for engagement with a hose 54, such as a hose that is connected to a balloon catheter structure. The piston 48 has a sealing member 50 thereon which seals with an internal wall 72 of the housing 42. The plunger 68 can be retracted to pull fluid through the hose 54 into the device 40, and can be extended (or pushed in) to push fluid out of the device 40 and into the hose 54.

Figure 2:
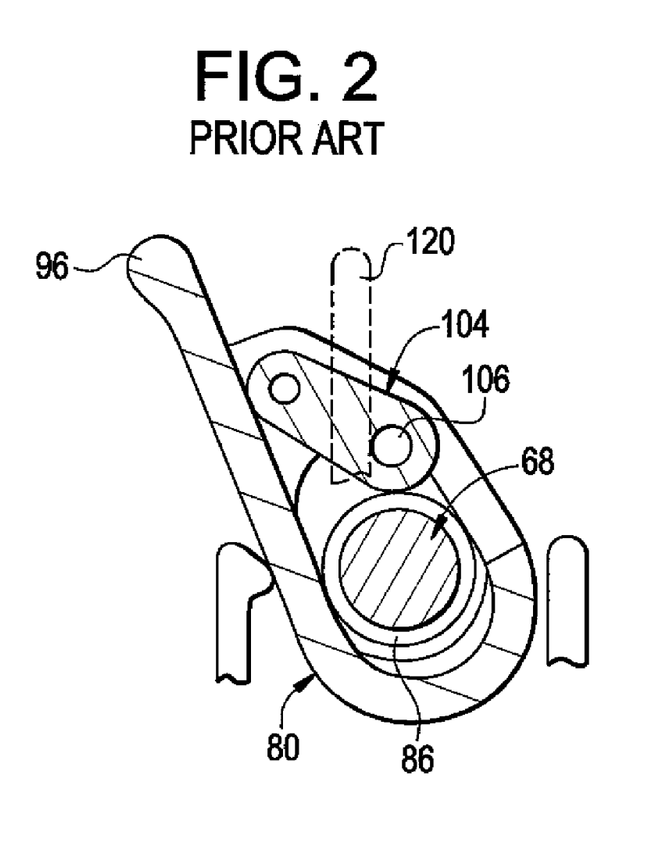
FIGS. 2 and 3 are enlarged views which illustrate two different positions of an actuating mechanism of the fluid displacement device which is shown in FIG. 1.
Figure 3:
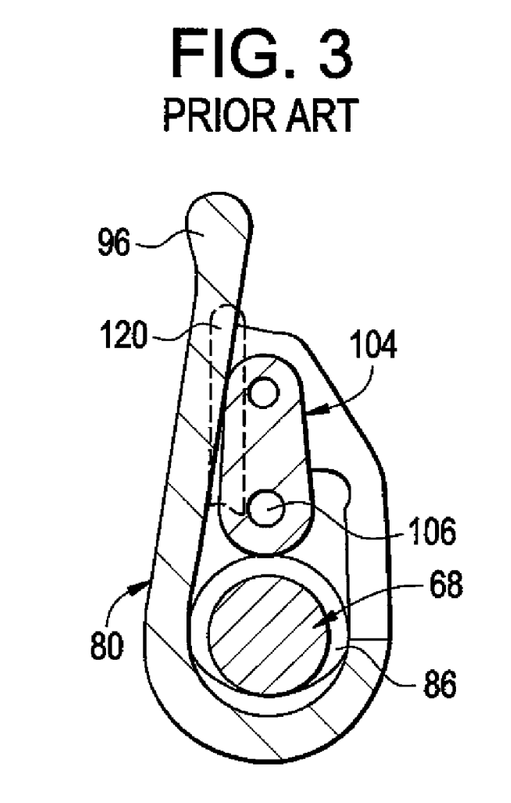

The plunger 68 can also be locked in place to prevent being pushed or pulled (i.e., to prevent macro movement of the plunger 68). Specifically, the device 40 includes a nut member 80 which can be moved into and out of engagement with a threaded portion 86 of the plunger 68. When the nut member 80 is not engaged with the threaded portion 86 of the plunger 68, as shown in FIG. 2, the plunger 68 can be extended or retracted (i.e., pushed or pulled) using macro movements. In contrast, when the nut member 80 is engaged with the threaded portion 86 of the plunger 68, as shown in FIG. 3, the plunger 68 is locked in place against macro movements, and can only be translated by using micro movements (i.e., by turning a knob 74 of the plunger 68).

To facilitate movement of the nut member 80, there are two link members 102, 104 which are engaged with the nut member 80 and which are retained on the device 40 by a pivot pin 106. The link members 102, 104 are positioned and configured to operate in tandem. As shown in FIGS. 2 and 3, the nut member 80 also includes a lever or grip portion 96 which can manipulated in order to shift the nut member 80, causing the nut member 80 to move into and out of engagement with the threaded portion 86 of the plunger 68. In order to move the nut member 80 into or out of engagement with the threaded portion 86 of the plunger 68, the link members 102, 104 must clear past ribs 120 (see FIGS. 2 and 3) which are provided on flanges 83 (see FIG. 1) which extend from the housing 42. Because the amount of force which is required to cause the link members 102, 104 to move past the ribs 120 depends on a plurality of part dimensions and tolerances, maintaining uniform detenting forces from one unit to the next, and from product line to product line, has proven challenging.

Another difficulty that can occur from time to time involves user convenience. Some users have found difficulty in reaching and engaging the lever 96 of the nut member 80 due to a combination of the manipulation required to perform the action and the operator's hand locations during certain procedures with the device 40, such as when the plunger 68 has been fully extended for vacuum and has to be locked into place. In such instances, the operator's hands can end up too far from the lever 96 to operate it without changing grip. During a disengage-withdraw plunger-reengage manipulation sequence (as occurs while drawing vacuum to pull down an interventional balloon after operation at pressure), users are forced to traverse the ribs 120 on the housing 42 twice by going one way and then back again the other direction in order to reengage the threaded plunger and hold it in a withdrawn position. Having to traverse the ribs 120 twice also occurs when manipulating to go from full vacuum or zero pressure to repressurization of the balloon.

Another disadvantage of the device 40 shown in the '959 patent relates to assembly. As shown in FIGS. 8-11 of the '959 patent, assembly requires alignment and sliding of the first link member 102 into the nut member 80, followed by upside down insertion of the second link member 104 into the nut member 80, and then 180 degree rotation of the second link 104 to align it with the first one 102. This requires manipulation and assembly time. Additionally, due to the need for free and independent rotation of the two link members 102, 104, it is not possible to be certain that these link members 102, 104 always stay in alignment with one another or are properly located in the nut member 80 to receive the pivot pin 106 during assembly.

Furthermore, precise longitudinal alignment is not generally possible with regard to the two link members 102, 104 and the nut member 80, and to both the pivot pin 106 and the threads 86 on the plunger 68. Specifically, each link member 102, 104 is free to pivot out of alignment slightly with the other and consequently allow the nut member 80 to slightly twist or deflect out of alignment with the plunger's axis during engagement and disengagement manipulations. Such twist is possible even though plunger 68 and pivot pin 106 are maintained in strict parallel alignment to one another. This undesirable deflection offers potential for a deleterious effect upon mating thread components resulting in uneven loading and occasional chipping of the most highly loaded threads during disengagement during maximum pressure use conditions.

OBJECTS AND SUMMARY

An object of an embodiment of the present invention is to provide an improved fluid displacement device.

Another object of an embodiment of the present invention is to provide an improved process for assembling a fluid displacement device.

Still another object of an embodiment of the present invention is to provide a fluid displacement device which is relatively easy to assemble.

Briefly, and in accordance with at least one of the foregoing objects, an embodiment of the present invention provides a fluid displacement device, particularly for use of the device to pressurize and depressurize catheters, or inject fluid, or aspirate fluid, or the like. The device includes a plunger which is displaceable through a housing, and an actuating mechanism which engages the plunger. The actuating mechanism includes a nut member and a unitary link member that provides an integral spring. The integral spring of the unitary link member provides that the nut member is biased into engagement with the threaded portion of the plunger. As such, the plunger is normally in the "locked" position, thereby preventing macro movements (i.e., pushing or pulling) of the plunger but allowing micro movements (i.e., turning) of the plunger. The actuating mechanism is configured to provide a press-to-release feature wherein the plunger is instantly releaseable by simply depressing a toggle lever of the nut member to overcome a restorative spring force provided by the integral spring of the unitary link member. Subsequently, the plunger can be translated using macro movements (i.e., by pushing or pulling the plunger).

Another aspect of the present invention provides a method of assembling a fluid displacement device. The assembly method includes assembling an actuating mechanism of the device by engaging a unitary link member with a nut member, whereby integral spring force of the unitary link member tends to hold the unitary link member in place on the nut member. A pin is then engaged with the unitary link member and the nut member, thereby forming an assembly. This assembly is then inserted in an opening in the housing and another pin is used to retain the assembly on the device.

The structure and method of assembling the fluid displacement device provide several advantages, as will be described more fully later hereinbelow.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which.

DESCRIPTION

While the invention may be susceptible to embodiment in different forms, there is shown in the drawings, and herein will be described in detail, a specific embodiment with the understanding that the present disclosure is to be considered an exemplification of the principles of the invention, and is not intended to limit the invention to that as illustrated and described herein.

A specific embodiment of the present invention comprises a fluid displacement device 200 which utilizes all the same components of the device disclosed in U.S. Pat. No. 6,796, 959, except for replacing the nut member 80 and link members 102, 104 of the '959 device with a unitary link 202, a nut member 204, and a pivot pin 206. As such, U.S. Pat. No. 6,796,959 is hereby incorporated herein by reference in its entirety.

Figure 4:
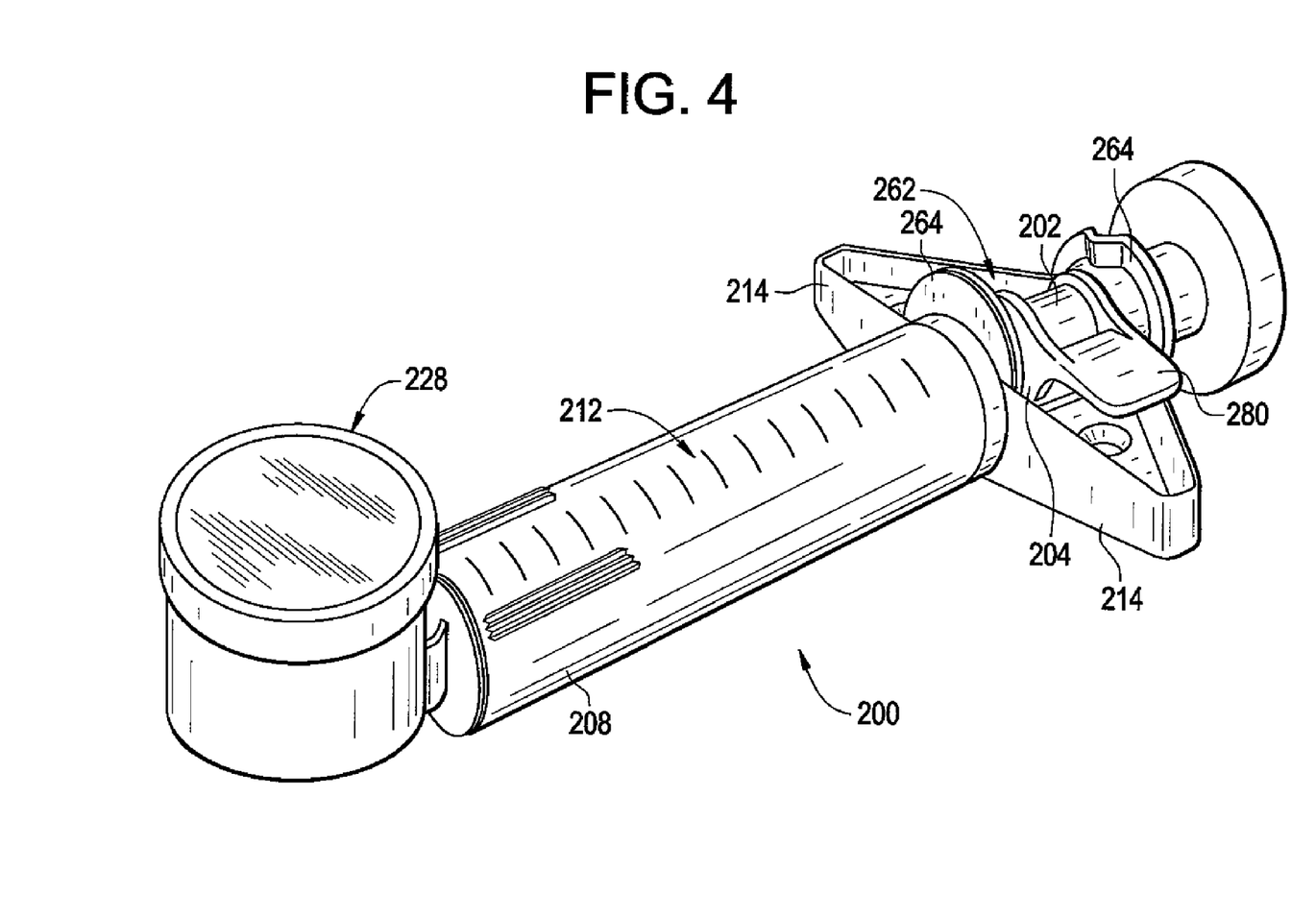
FIG. 4 is a perspective view of a fluid displacement device which is in accordance with an embodiment of the present invention.
Figure 5:
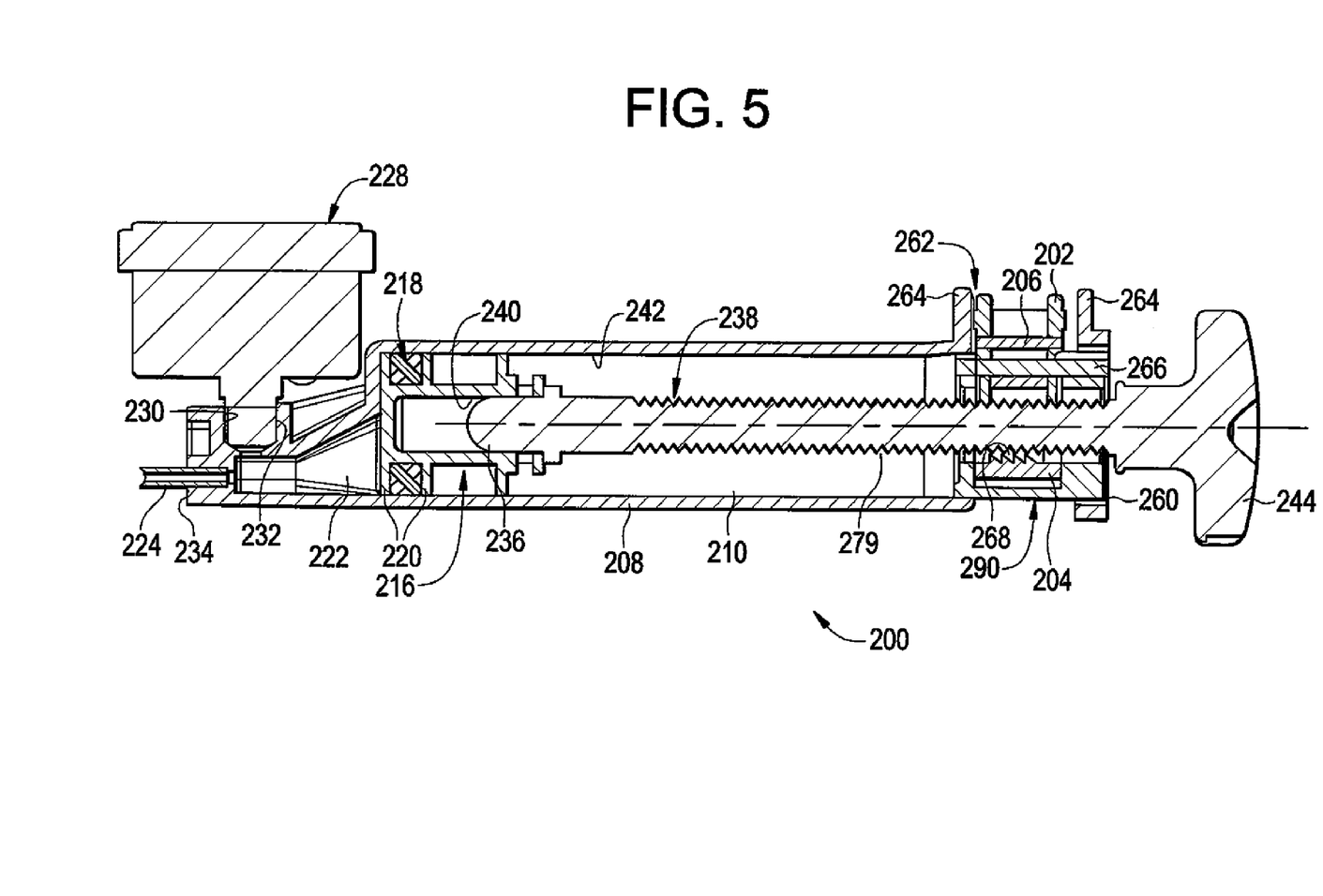
FIG. 5 is a cross-sectional view of the fluid displacement device shown in FIG. 4.
Figure 6:
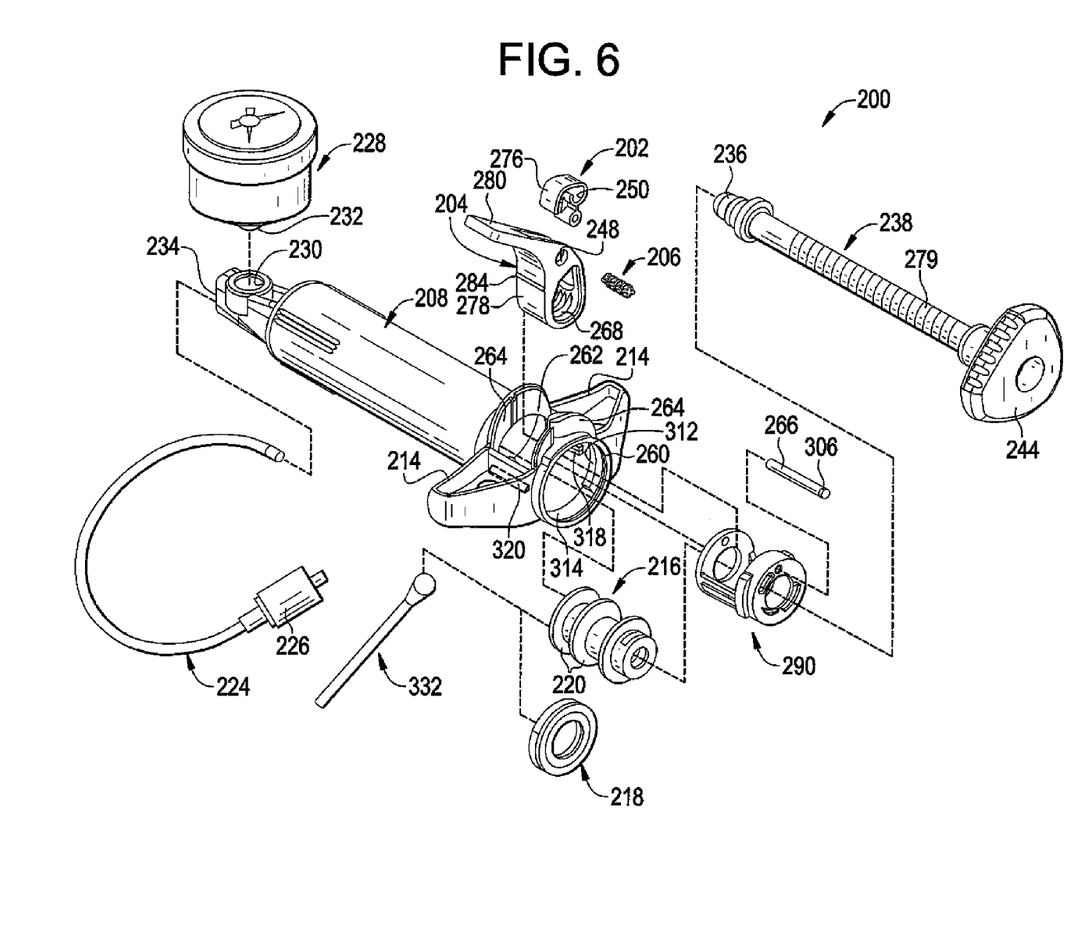
FIG. 6 is an exploded perspective view of the fluid displacement device shown in FIGS. 4 and 5.

As shown in FIGS. 4-6, the fluid displacement device 200 which is in accordance with a specific embodiment of the present invention has a generally cylindrical syringe body or housing 208 which provides a fluid displacement chamber 210 (see specifically FIG. 5). Preferably, the housing 208 is transparent thereby facilitating the viewing of fluid in the fluid displacement chamber 210 during fluid aspiration or dispensing. The housing 208 is formed of plastic, and may be molded from polycarbonate or another type of resin. The housing 208 has volumetric indicia thereon, such as at location 212 indicated in FIG. 4, so that a physician can readily determine the volume of fluid contained in the chamber 210. As shown, handles 214 are provided on the housing 208 to facilitate gripping of the device 200 and operation thereof.

A piston 216 is slidably displaceable within the fluid displacement chamber 210 (i.e. in the housing 208). A sealing member 218, such as a quad ring, is disposed on the piston 216. As shown in FIG. 5, preferably the sealing member 218 is disposed between two walls 220 on the piston 216. As will be described more fully later hereinbelow, a lubricant may be used to place the sealing member 218 on the piston 216. The sealing member 218 is configured for pressure retention and the prevention of leakage of fluid past the piston 216 in the fluid displacement chamber 210. The housing 208 includes a fluid conduit 222 which is in communication with the fluid displacement chamber 210. The fluid conduit 222 is also in communication with a hose 224 that is connected to, for example, balloon catheter structure (not shown), a fluid supply reservoir (not shown) or some other suitable structure depending on the application. As shown in FIG. 6, a connector 226 may be provided on the hose 224, between the fluid conduit 222 and the balloon catheter.

As shown in FIG. 5, the fluid conduit 222 also communicates with a pressure gauge assembly 228. Preferably, the pressure gauge assembly 228 is engaged directly with the housing 208, such as threadably engaged with a threaded bore 230 (see FIGS. 5 and 6) thereon. To this end, the pressure gauge assembly 228 is provided with a threaded portion 232 which threadably engages the threaded bore 230 on the housing 208. An adhesive may be provided between the threaded portion 232 and the threaded bore 230 to lockingly and sealingly engage the parts together. As shown in FIGS. 5 and 6, the threaded bore 230 is provided generally proximate an end 234 of the housing 208 such that, when installed, the pressure gauge assembly 228 is disposed generally proximate a distal end of the device. The pressure gauge assembly 228 is configured to provide a physician with an indication of the pressure in the fluid conduit 222 and balloon catheter. The pressure gauge assembly 228 can be of any suitable type for either angioplasty or for other employment of the device 200. The fact that the device 200 is configured such that the pressure gauge assembly 228 engages directly with the housing 208 provides increased visibility proximate the distal end of the device. Such visibility becomes important when a physician is to purge all the air bubbles from the fluid displacement chamber 210 before using the device 200 to dispense fluid. Alternatively, the device 200 can be configured such that the pressure gauge assembly 228 engages a clamping cover such as is shown and described in U.S. Pat. No. 5,713,242, which has been incorporated herein by reference in its entirety.

As best shown in FIG. 5, the piston 216 is mounted on an unthreaded pilot nose end 236 of a plunger 238. The pilot nose end 236 is configured to freely rotate in a central journal cavity 240 of the piston 216. The piston 216 is mounted on the pilot nose end 236 of a plunger 238 in a snap-action, interference coupling which prevents the pilot nose end 236 from withdrawing or backing out of the central journal cavity 240 of the piston 216 when the plunger 238 is retracted to aspirate fluid into the fluid displacement chamber 210. The pilot nose end 236 is freely rotatable relative to the coupled piston 216. As such, when the plunger 238 is rotated (i.e., during micro movements), the piston 216 does not rotate along with the plunger 238, but rather linearly advances or retracts in the housing 208. The fact that the piston 216 does not rotate tends to prevent any leakage of pressurized fluid from the fluid displacement chamber 210 between the sealing member 218 and an internal wall 242 (see FIG. 5) of the housing 208. As shown in FIGS. 4-6, the plunger 238 preferably includes an integral palm knob 244 which facilitates movement of the plunger 238 as will be described in more detail hereinbelow.

The device includes an actuating mechanism 246 which is normally biased into engagement with the plunger 238, but which can be actuated out of engagement with the plunger 238. When the actuating mechanism 246 (see FIG. 7) is biased into engagement with the plunger 238, macro movements of the plunger 238 are not generally possible, only micro movements are. When macro movements are prevented, the plunger 238 cannot be pushed into or pulled out of the housing 208 (i.e., to displace a large amount of fluid quickly). Instead, the plunger 238 can only be translated by rotating its knob 244 (i.e., to displace fluid slowly, with more precision). On the other hand, when the actuating mechanism 246 is actuated out of engagement with the plunger 238, macro movements of the plunger 238 are possible. When macro movements are possible, the plunger 238 can be pushed into or pulled out of the housing 208.

Figure 7:
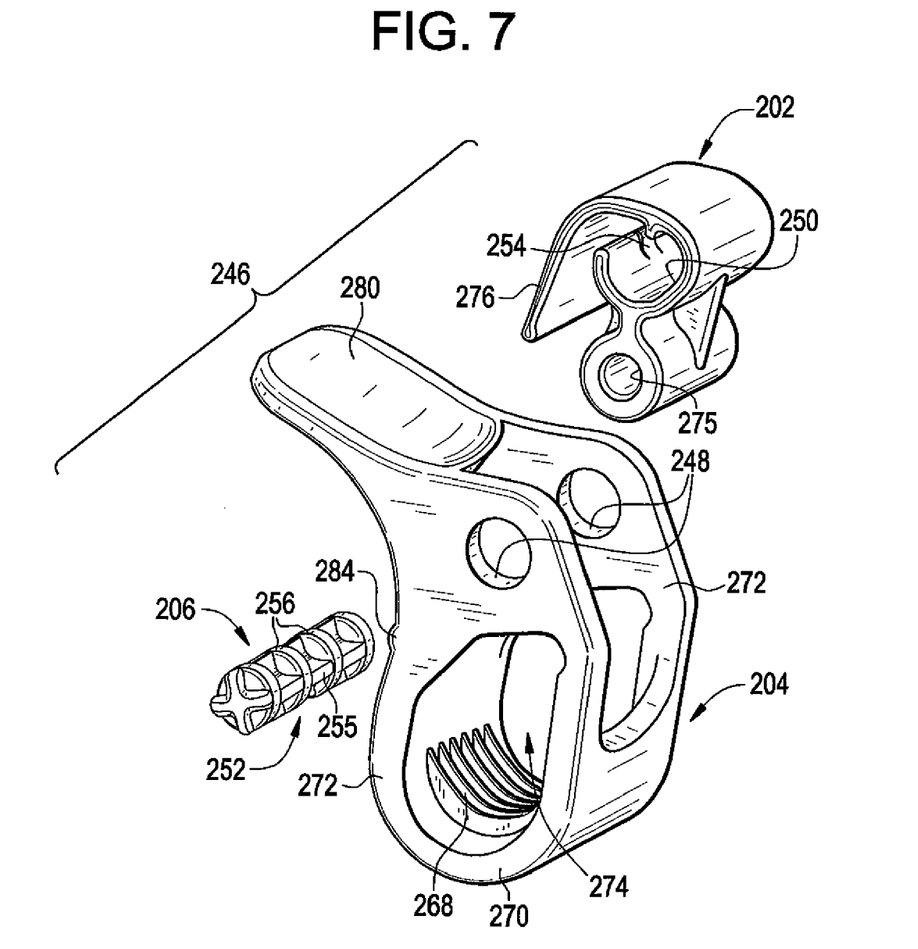
FIG. 7 is an enlarged exploded perspective view of a portion of the fluid displacement device shown in FIGS. 4-6, specifically an actuating mechanism thereof.
Figure 18:
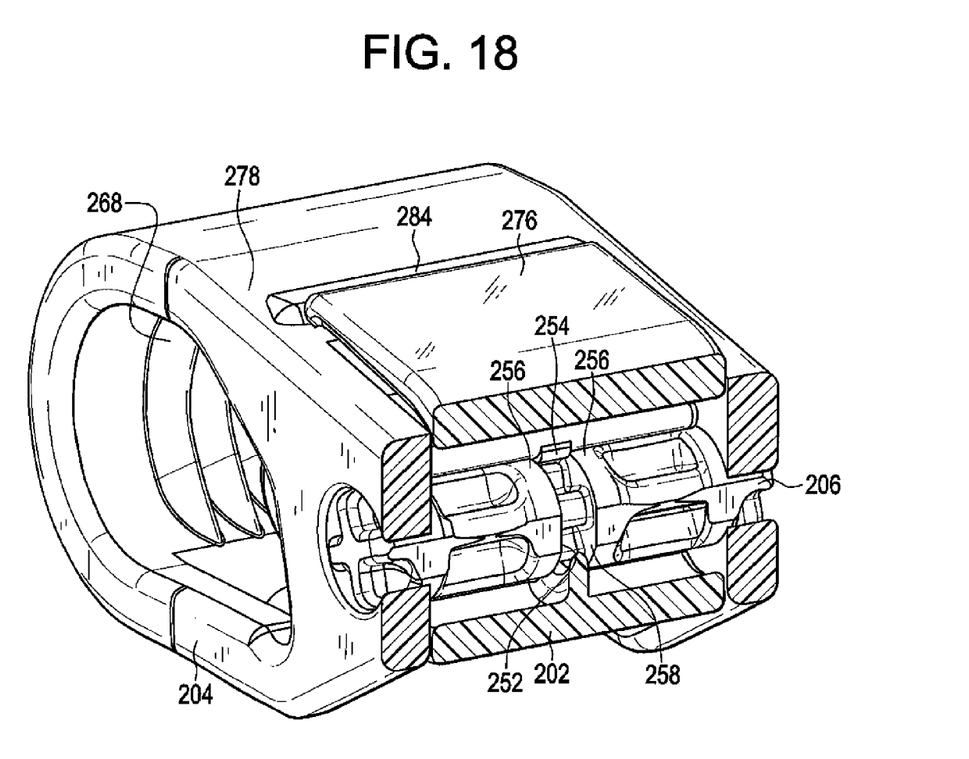
FIG. 18 is a partial cross-sectional view of the actuating mechanism of the fluid displacement device shown in FIGS. 4-6, showing an internal rib feature.

As shown in, for example, FIG. 7, the actuating mechanism 246 comprises a unitary link 202, a nut member 204, and a pivot pin 206. The pivot pin 206 extends through holes 248 on the nut member 204 and though a passageway 250 in the unitary link 202, thereby effectively retaining the unitary link 202 on the nut member 204 and forming an assembly. As shown in FIG. 18, the pivot pin 206 is preferably provided with a reduced diameter middle portion 252 which receives a central rib 254 within the unitary link 202 which locks the pivot pin 206 in place relative to the unitary link 202. Specifically, the pin 206 has a cruciform shape with lower cruciform members 255 being provided between two central disk features 256. These lower cruciform members 255 effectively form a groove 258 on the pivot pin 206, wherein the raised rib 254 in the unitary link 202 is configured to catch in the groove 258 on the pivot pin 206 and hold the pivot pin 206 in place.

As shown in FIGS. 4 and 5, the overall assembly is disposed in the housing 208, generally near a rearward end 260 of the housing 208. Specifically, as shown in FIGS. 4-6, the actuating mechanism 246 is preferably disposed in an aperture 262 in the housing 208, where the aperture 262 is provided between a pair of spaced flanges 264, and the actuating mechanism 246 is mounted on the device 200 viz-a-viz a pin 266, which is preferably made of metal.

As viewed in FIGS. 5-7, the nut member 204 has threads 268 which are formed in a lower base portion 270, and the nut member 204 includes an upstanding, bifurcated portion which provides a pair of spaced, elongate arm or mounting portions 272 (see specifically FIG. 7). The mounting portions 272 in effect define carriage structure, and are generally integral with the threads 268. Each of the mounting portions 272 has an aperture 274 therein, through which the plunger 238 extends (see specifically FIGS. 5, 8 and 9), as well as a hole 248 for receiving the pivot pin 206.

Figure 8:
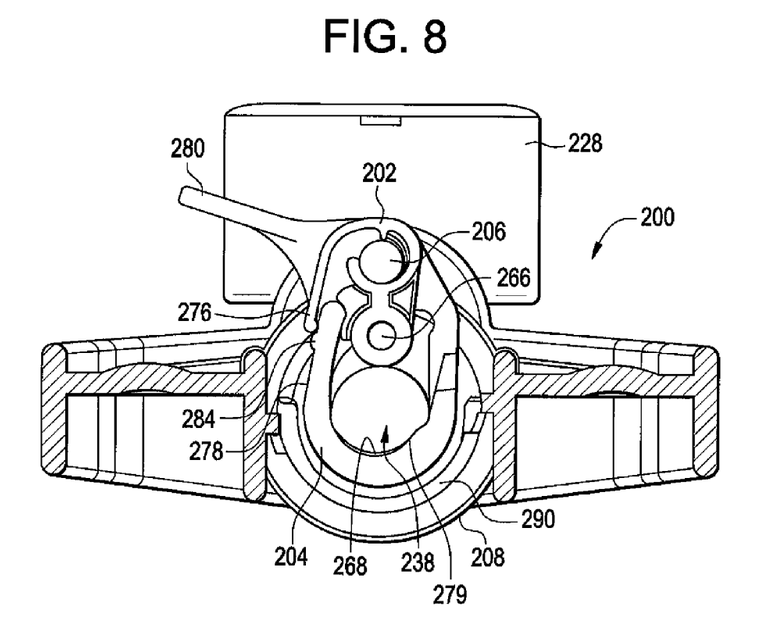
FIG. 8 is a partial cross-sectional view of the fluid displacement device shown in FIGS. 4-6, showing the actuating mechanism biased into engagement with a plunger of the device.

FIG. 8 illustrates how it is that the nut member 204 is biased into engagement with the plunger 238. Specifically, a spring finger portion 276 of the unitary link 202 engages an external surface 278 of the nut member 204, and this contact along with the rigidity of the spring finger portion 276 of the unitary link 202 generates a restorative spring force which tends to keep the nut member 204 in the position shown in FIG. 8, wherein the threads 268 on the nut member 204 are engaged with threads 279 of the plunger 238. In this position, the plunger 238 cannot be pushed into or pulled out of the housing 208 using macro movements. Instead, the plunger 238 must be translated using only micro movements, i.e. by turning its knob 244, causing the threads 279 of the plunger 238 to worm along the threads 268 of the nut member 204. As described above, the pilot nose end 236 of the plunger 238 is configured to freely rotate in the central journal cavity 240 of the piston 216. Hence, rotation of the plunger 238 while the threads 268 of the nut member 204 are engaged with the threaded portion 279 of the plunger 238 does not cause the piston 216 to rotate in the fluid displacement chamber 210 in the housing 208, but instead causes the piston 216 to merely slide in the housing 208.

To provide the integral spring feature (i.e., the spring finger 276) of the unitary link 202, the unitary link 202 is made of a material that has both excellent compressive strength and good stiffness coupled with a high degree of elasticity to allow deflection without plastic deformation or breakage.

Acetal resin, commercially known as Delrin or Celcon for instance, offers these properties, but to a lesser degree than do Nylon or Polypropylene materials. Acetel is often preferred for polymer spring applications due to its ability to withstand large degrees of deflection without plastic deformation or fracture along with its inherent lubricity, hardness and resistance to environmental stress, cracking and wear. In the application disclosed herein, the part must be able to tolerate pivoting and sliding against mating components of Nylon and metal for which Acetal is known to perform particularly well.

By virtue of the return spring force being sufficient to keep the device 200 in a plunger-engaged, default position, ribs (identified with reference numeral 120 in FIGS. 2 and 3, herein) such as is shown in U.S. Pat. Nos. 5,713,242 and 6,796,959, and the additional user effort which is required to overcome them, are no longer necessary. When the nut member 204 is biased into engagement with the plunger 238 as shown in FIG. 8, the nut member 204 is in an "over-center" locking position which ensures that any slight motion of the nut member 204 which could be induced by fluid pressure in the fluid displacement chamber 210 imposed on piston 216 results in tighter engagement of the plunger 238 and nut member 204 rather than any tendency for loosening or disengagement thereof.

The nut member 204, and specifically the threads 268 thereof, is selectively disengageable from the plunger 238 in order to permit manual rapid displacement of the plunger 238 and piston 216, for example, for aspiration of saline solution into the fluid displacement chamber 210 from a fluid supply reservoir (not shown) which may be connected to the hose 224 or in which connector 226 may be immersed. The disengagement of the nut member 204 from the plunger 238 also enables rapid advancement of the plunger 238 and piston 216, for example, to discharge solution through the hose 224 to inflate an angioplasty balloon (not shown) which has been previously positioned within a blood vessel or heart valve using a balloon catheter. Rapid retraction of the plunger 238 and piston 216 may also enable swift aspiration of fluid into the fluid displacement chamber 210 for rapid deflation of an angioplasty balloon. Also, prior to connection to the catheter, the plunger 238 may be operated to insure that all air bubbles have been eliminated from the fluid which is contained in the fluid displacement chamber 210.

Figure 9:
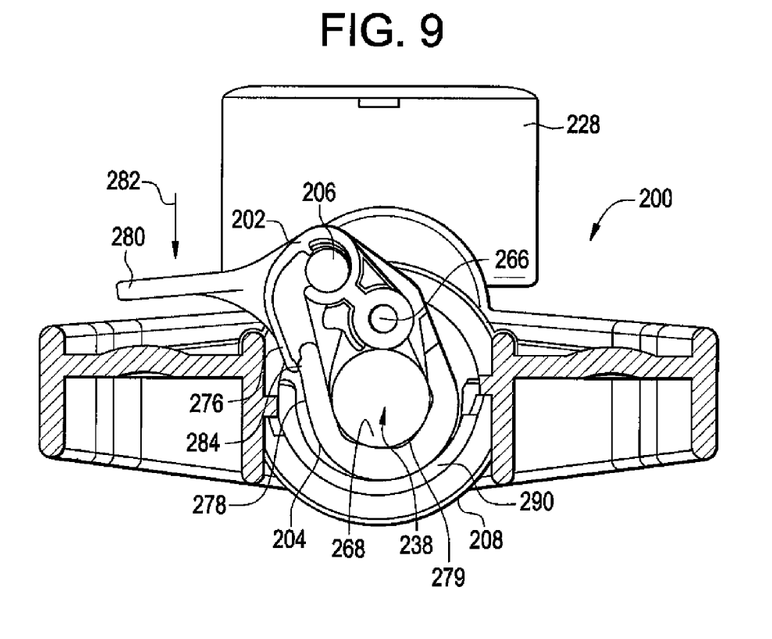
FIG. 9 is a partial cross-sectional view of the fluid displacement device shown in FIGS. 4-6, showing the actuating mechanism being actuated such that it has moved out of engagement with the plunger.
Figure 10:
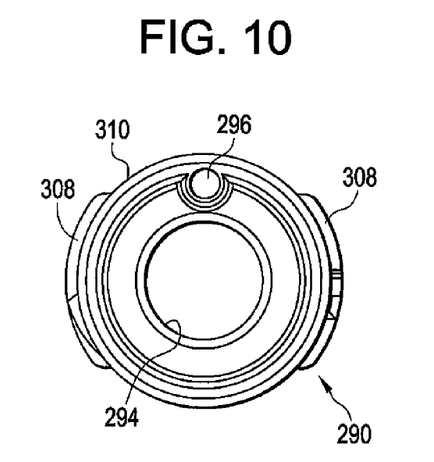
FIG. 10 is a front, elevational view of a carrier member component of the fluid displacement device shown in FIGS. 4-6.

In order to facilitate the selective disengagement of the threads 268 of the nut member 204 with the threaded portion 279 of the plunger 238, as shown in FIG. 9, the nut member 204 is provided as having a lever 280 (see FIGS. 4, 8 and 9), wherein disengagement of the nut member 204 is achieved by pressing down on the lever 280 (as represented by arrow 282 in FIG. 9). Pressing down on the lever 280, as shown in FIG. 9, causes the assembly to traverse, and causes the spring finger portion 276 of the unitary link 202 to ride along the external surface 278 of the nut member 204 and be deflected outwardly. Displacement of the nut member 204 is preferably guided along a translating motion between the positions shown in FIGS. 8 and 9. The motion of the nut member 204 in moving between the positions of FIGS. 8 and 9 is in actuality that of a diminishing curved path and, as such, is not truly linear. When the lever 280 of the nut member 204 is pressed down, the spring finger portion 276 of the unitary link 202 becomes flexed, generally creating a bias of the assembly back into the position shown in FIG. 8. As such, releasing the lever 280 causes the assembly to return to the position shown in FIG. 8. FIG. 8 illustrates the normal, non-actuated position of the nut member 204 in which the threads 268 of the nut member 204 are biased into engagement with the threaded portion 279 of the plunger 238, thereby locking the plunger 238 with regard to macro movements. However, micro movements of the plunger 238 are possible by rotating its knob 244, causing the threads of the plunger 238 to worm along the threads 268 on the nut member 204.

In contrast, FIG. 9 illustrates what occurs when a user presses down on the lever 280 of the nut member 204. As shown, this causes the nut member 204 to traverse, causing the threads 268 of the nut member 204 to become disengaged from the threaded portion 279 of the plunger 238. In such a position, the plunger 238 may be axially translated in the fluid displacement chamber 210 by pushing the plunger 238 forward into the housing 208, or by pulling the plunger 238 back out of the housing 208. In other words, pushing or pulling the plunger 238 is prevented when the nut member 204 is engaged with the plunger 238. However, pushing the lever 280 of the nut member 204 down causes the nut member 204 to disengage the plunger 238, thereby allowing the plunger 238 to be pushed or pulled.

Although only optional, the nut member 204 preferably includes a cam feature 284 as shown in FIGS. 6-9. When the lever 280 of the nut member 204 is pushed down, the spring finger 276 of the unitary link 202 must ride up on the cam 284, as shown in FIG. 9. The cam 284 works to increase the closing force (i.e., the tendency for the overall actuating mechanism 246 to return to the position shown in FIG. 8) and provide a definitive location to assure that the at-rest position (see FIG. 8, wherein the lever 280 of the nut member 204 is not being pressed) is fully achieved by the nut member 204 rather than allowing this position to be indeterminate as may be the case without the cam feature. The cam feature 284 provides both auditory and tactile feedback to the user with regard to whether the nut member 204 is engaged with the plunger 238. To provide more definitive feedback, the cam feature 284 may be configured to provide a sharp step for spring finger 276 to ride over and subsequently return over. This provides that the spring finger 276 will snap over cam 284, providing more definitive auditory and tactile feedback to the user of the released or engaged position of threads 268 with plunger 238.

As shown in FIGS. 5, 6, 8 and 9, preferably the device 200 includes a carrier member 290 that is received in the housing 208, much like the device shown in U.S. Pat. No. 6,796,959. As shown in FIGS. 6 and 10-17, the carrier member 290 may be provided in the form of a generally hollow, generally cylindrical part. The carrier member 290, like the housing 208, may be formed of plastic. In fact, the carrier member 290 and the housing 208 may be formed of the same resin.

As shown in FIGS. 5, 6, 10, 11, 15 and 17, the carrier member 290 has spaced-apart walls 298, 300, and the walls 298, 300 are provided with apertures 294 through which the plunger 238 extends, as well as apertures 296 which retain the pin 266 that secures the actuating mechanism 246 to the device 200. More specifically, the carrier member 290 supports the pin 266, and the pin 266 extends through a bore 275 in the unitary link 202, thereby providing that the pin 266 generally retains the actuating mechanism 246 on the device 200.

Figure 11:
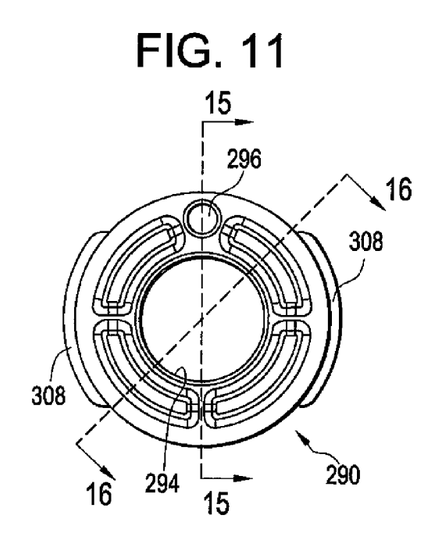
FIG. 11 is a rear, elevational view of the carrier member.
Figure 12:
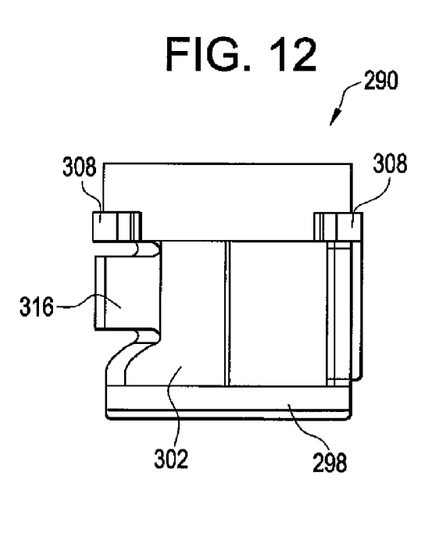
FIG. 12 is a top, plan view of the carrier member.
Figure 13:
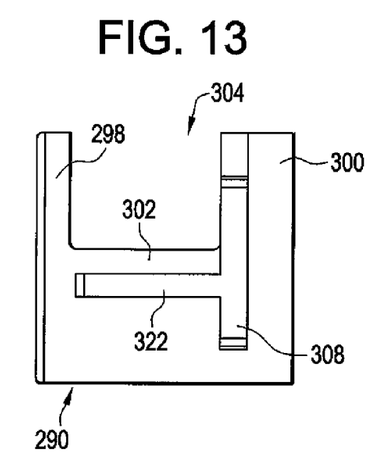
FIG. 13 is a side, elevational view of the right side of the carrier member.
Figure 14:
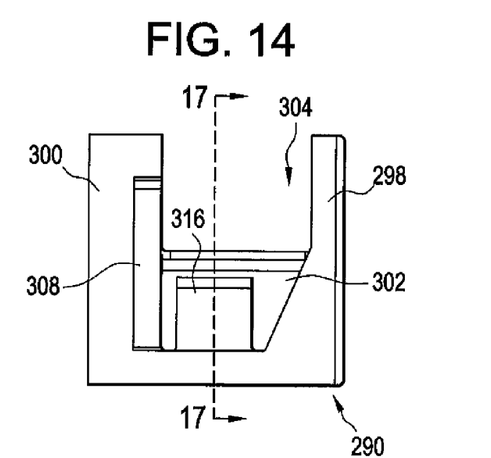
FIG. 14 is a side, elevational view of the left side of the carrier member.
Figure 15:
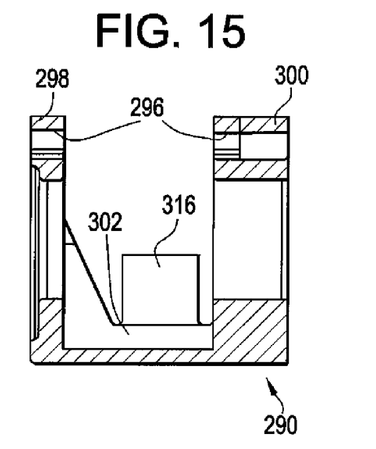
FIG. 15 is a cross-sectional view of the carrier member, taken along line 15-15 of FIG. 11.
Figure 16:
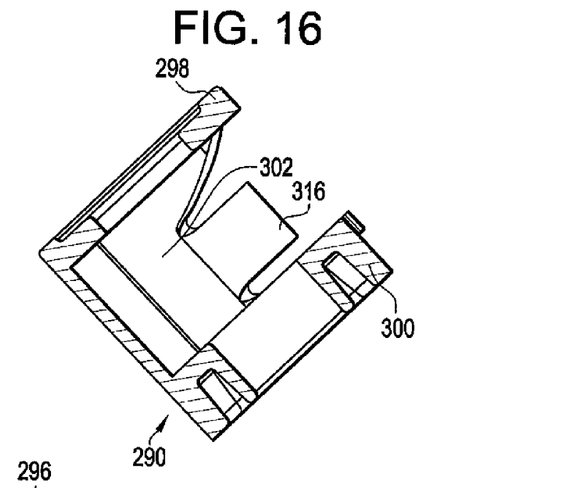
FIG. 16 is a cross-sectional view of the carrier member, taken along line 16-16 of FIG. 11.
Figure 17:
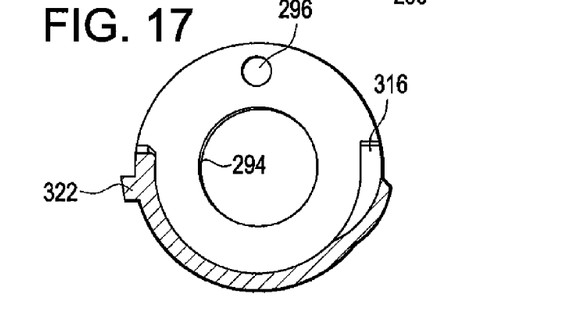
FIG. 17 is a cross-sectional view of the carrier member, taken along line 17-17 of FIG. 14.

As shown in FIG. 6, wall 298 defines the front surface of the carrier member 290 (see also FIG. 10, which provides a view of the front of the carrier member 290), and wall 300 defines the rear surface of the carrier member 290 (see also FIG. 11, which provides a view of the rear of the carrier member 290). A partial wall 302 extends between the front and rear walls 298 and 300 of the carrier member 290. A cut out 304 is defined between the walls 298 and 300, and the nut member 204 is disposed in the cut out 304 (see FIG. 5). The pin 266 extends through the apertures 296 provided in the carrier member 290, and the carrier member 290 generally retains the pin 266 such that the pin 266 does not readily move axially. As shown in FIG. 6, the pin 266 may be provided with a knurled end portion 306 which assists in preventing the pin 266 from translating axially once it is installed in the carrier member 290.

As shown in FIGS. 6 and 10-15, protruding surfaces 308 are provided on an external surface 310 of the carrier member 290, generally proximate the rear end of the carrier member 290. Corresponding inward facing flanges 312 are provided in the housing 208, at the rearward end 206 thereof, for receiving interruptions between protruding surfaces 308 provided on the carrier member 290. Preferably, the flanges 312 in the housing 208 and the interruptions between protruding surfaces 308 on the carrier member 290 provide that the carrier member 290 can be inserted in a bore 314 in the end 260 of the housing 208, and then rotated to secure the carrier member 290 in the housing 208. Specifically, the carrier member 290 and housing 208 are configured such that the carrier member 290 is installable through the rear portion of the housing 208 in the bore 314 in the housing 208 via a quarter-turn bayonet arrangement, wherein the carrier member 290 is axially inserted in the bore 314 and then given a one-quarter turn to lock the carrier member 290 in place.

The carrier member 290 includes a latching finger 316 which is formed as part of the partial wall 302 which extends between the front and rear walls 298, 300 of the carrier member 290. The latching finger 316 preferably engages an inwardly extending rib 318 provided on an internal wall of the housing 208 (see FIG. 6). Specifically, the latching finger 316 engages and clears the inwardly extending rib 318 on the housing 208 in a manner which generally locks the carrier member 290 in place in the bore 314 in the housing 208. Preferably, the latching finger 316 and inwardly extending rib 318 are configured such that an audible noise is produced as the latching finger 316 engages and clears the inwardly extending rib 318. The noise is loud enough to provide an audible indication to an assembler of the device 200 that the carrier member 290 is fully installed in the bore 314.

Preferably, another inwardly extending rib 320 is provided on the internal wall of the housing 208 exactly opposite rib 318 (i.e. 180 degrees from rib 318, along the interior wall of the housing 208). A protruding surface 322 is provided on the external surface 310 of the carrier member 290, generally extending from protrusion 308 of the carrier member 290 toward the front end of the carrier member 290. When the carrier member 290 is inserted in the bore 314, the protruding surfaces 308 abut the proximal ends of ribs 318 and 320 (see FIGS. 5 and 8-10) of the housing 208 to prevent the carrier member 290 from installing too far axially into the bore 314. In other words, engagement of the protruding surfaces 308 with ribs 318 and 320 limits axial travel of the carrier member 290 in the bore 314 during installation. Once the protruding surface 308 contacts ribs 318 and 320, the carrier member 290 is rotated such that it becomes fully installed. Preferably, not only does the latching finger 316 of the carrier member 290 engage and clear the inwardly extending flange 318 on the housing 208, but the protruding surface 308 on the carrier member 290 engages behind the opposite inwardly extending flanges 312 on the internal surface of the housing 208. When the carrier member 290 is fully installed in the bore 314, the carrier member 290 cannot be readily axially withdrawn from the bore 314, nor can the carrier member 290 be readily rotated in either rotational direction relative to the housing 208. When the carrier member 290 is properly installed in the housing 208, the cut out 304 in the carrier member 290 is generally aligned with the aperture 262 in the housing 208.

The nut member 204, unitary link 202 and pin 206 (i.e., the actuating mechanism 246) is received in the cut out 304 in the carrier member 290 and the aperture 262 in the housing 208 such that the lever 280 of the nut member 204 generally extends out the aperture 262 in the housing 208 for easy access, as shown in FIGS. 4, 8 and 9. The carrier member 290 is securably engaged relative to the housing 208, and the pin 266 which secures the actuating mechanism 246 is retained by the carrier member 290.

The carrier member 290 is configured to withstand in-use forces as the plunger 238 is translated forward in the fluid displacement chamber 210. The carrier member 290 permits the device 200 to be assembled from the rear of housing 208 (i.e. is rear loaded), as will be described more fully later hereinbelow in connection with describing assembly of the device. Additionally, as shown in FIG. 5, the carrier member 290 provides that a distance from a center line of the plunger 238 to an internal wall 242 of the housing 208 can be greater than a distance from the center line of the plunger 238 to the pin 266.

Still further, the design of the device 200, by including the carrier member 290, provides that many of the parts are universal such that they are compatible with devices of different sizes. Specifically, the nut member 204 and plunger 238 may be used in association with different sized devices, specifically devices with different sized fluid displacement chambers. The carrier member 290 shown in the Figures is designed to be used with fluid displacement chambers which are as large as that shown in the Figures or which are smaller than that shown in the Figures. Of course, a larger or smaller sized device can be provided than is depicted in the Figures, which are not to scale.

Despite all the advantages that are provided by having the device include the carrier member 290, the device can instead be provided as not having a carrier member, such as is disclosed in U.S. Pat. No. 5,713,242, which has been incorporated herein by reference.

Regardless, the device 200 is configured such that a user need not change grip of the device 200 during use. The lever 280 of the nut member 204 just needs to be pressed to effect plunger 238 disengagement, and ribs (identified with reference numeral 120 in FIGS. 2 and 3) need not be overcome to move back and forth between a plunger-engaged and a plunger-disengaged position. Additionally, release of the lever 280 provides instant plunger 238 re-engagement. By virtue of the return spring force provided by the spring finger 276 of the unitary link 202 being sufficient to keep the device 200 in a plunger-engaged default state (as shown in FIG. 8), detents or ribs on the housing 208 and additional user effort required to overcome them are no longer necessary.

A method of assembling the device 200 will now be described, in the situation where the device does, in fact, include a carrier member 290 such as disclosed in U.S. Pat. No. 6,796,959. To assemble the device 200, hose 224 may be affixed to the housing 208. Then, the pressure gauge assembly 228 is threadably engaged with the housing 208. Subsequently, the sealing member 218 is fit onto the piston 216. To facilitate this, a lubricant can be used as illustrated by applicator 332 shown in FIG. 6. Then, the piston 216 is slipped into bore 314 in the housing 208 (i.e. from right-to-left in FIG. 5). In other words, the piston 216 is rear loaded into the device 200. Then, the carrier member 290 is installed on the housing 208, also from the rear portion of the housing 208. As described above, this installation may be via a quarter-turn bayonet style installation wherein the carrier member 290 is axially inserted into the bore 314 and then is rotated a quarter-turn to lock the carrier member 290 in place relative to the housing 208. As described above, preferably the locking finger 316 on the carrier member 290 emits a snapping or clicking sound once the carrier member 290 is fully and properly installed. When the carrier member 290 is properly installed in the housing 208, the cut out 304 in the carrier member 290 is generally aligned with the aperture 262 in the housing 208. Subsequently, the actuating mechanism 246 can be installed in the aperture 262. However, before the actuating mechanism 246 is installed, the actuating mechanism 246 must be assembled.

To assemble the actuating mechanism 246, the unitary link 202 is clipped onto the nut member 204, and the pivot pin 206 is used to secure the unitary link 202 to the nut member 204. Even before the pivot pin 206 is used to secure the unitary link 202 to the nut member 204, the unitary link 202 tends to stay in place relative to the nut member 204 due to the spring force provided by the integral spring feature 276 of the unitary link 202. To secure the unitary link 202 to the nut member 204, the pivot pin 206 is pushed through one hole 248 on the nut member 204, though a passageway 250 in the unitary link 202, and into the other hole 248 in the nut member 204, thereby effectively forming an assembly. As shown in FIG. 18, when the pivot pin 206 is in place, a central rib 254 in the unitary link 202 engages a reduced diameter middle portion 252 of the pivot pin 206, thereby locking the pivot pin 206 in place relative to the unitary link 202. Once the actuating mechanism 246 is assembled, the actuating mechanism 246 can be inserted into the aperture 262, and the pin 266 used to secure the actuating mechanism 246.

After the actuating mechanism 246 has been installed on the device 200, the lever 280 of the actuating mechanism 246 is pushed down, and the plunger 238 is axially inserted into the rear end 260 of the housing 208 into engagement with the piston 216. Specifically, the nose end 236 of the plunger 238 is inserted through bore 314, through the bore 274 provided in the nut member 204, and into snap-fit engagement with the piston 216 within the fluid displacement chamber 210. Thereafter, the lever 280 of the actuating mechanism 246 can be released, and device 200 is thereafter operable.

As described hereinabove, assuming the device is provided in accordance with U.S. Pat. No. 6,796,959, and includes a rear-loading carriage member 290, the device is configured to be assembled from the rear. Specifically, both the piston 216 and carrier member 290 are installed in the rear of the housing 208. By providing that the device is assembled from the rear, the housing 208 can be provided as a single, integral piece. The front portion of the housing 208 can be molded as part of the housing 208, and no extra fittings or clamping covers need to be used to mount the gauge 228 to the housing 208. The gauge 228 can be engaged directly with the housing 208. Hence, the design has fewer parts and requires less labor than if the device were provided as being consistent with that which is shown in U.S. Pat. No. 5,713,242. Additionally, there is no issue with regard to sealing the front of the device 200 because the front portion of the device 200 is integral with the remainder of the housing 208. Moreover, visibility at the front of the device 200 is improved, and this is advantageous to a user who is attempting to prime the device 200 before use by purging all the air bubbles from the chamber 210. By providing that the housing 208 is molded as a single piece, the housing 208 can be manufactured in a single molding operation, thereby reducing the cost of the components and the molds, creating less waste and streamlining the production and assembly process.

Furthermore, the design of the device 200, by including the carrier member 290, provides that many of the parts are universal such that they are compatible with devices of different sizes. For example, the carrier member 290 shown in the FIGURES is designed to be used with fluid displacement chamber 210s which are as large as that shown in the FIGURES or which are smaller than that shown in the FIGURES.

Notwithstanding the fact that using a carrier member 290 provides several advantages, using a carrier member 290 is not imperative to employing the present invention. As discussed above, the present invention can be used in association with, for example, the device disclosed in U.S. Pat. No. 5,713,242, which does not include a carriage member.

Benefits derived from the actuating mechanism 246 disclosed herein include elimination of a pair of links, such as disclosed in U.S. Pat. Nos. 5,713,242 and 6,796,959, in exchange for a single unitary link 202 that, by virtue of its integrated spring form, is designed to be self-fixturing through its ability to be clipped precisely in position to the mating nut member 204 and thereby retain itself perfectly for receiving insertion of the pivot pin 206 as well as the pin 266 which secures the actuating mechanism 246 to the device 200. With the designs described in U.S. Pat. Nos. 5,713,242 and 6,796,959, assembly required alignment and sliding of a first link into its receiving bore followed by up-side-down insertion of a second link onto its receiving bore, then subsequent 180 degree rotation of the second link to align it with the first one. Much more manipulation and thereby assembly time was involved. By comparison, assembly of the actuating mechanism 246 disclosed herein simply involves clipping the unitary link 202 onto the nut member 204, where it retains itself by virtue of its integral leaf spring element 276, and then inserting the pivot pin 206 through both the nut member 204 and the unitary link 202 to hold the assembly together. As discussed above, the pivot pin 206 is preferably made with a reduced diameter middle portion 252 which receives a central rib 254 that is provided in the unitary link 202, which locks the pin 206 in place. This stable, locked together sub-assembly eases subsequent assembly of the inflation device because there are no loose or floppy parts requiring further alignment before the pin 266 is used to mount the actuating mechanism 246 on the device 200. Additionally, the unitary link 202 becomes automatically positioned to receive the pins 206 and 266. In contrast, with the devices disclosed in U.S. Pat. Nos. 5,713,242 and 6,796,959, due to the need for free and independent rotation of the pair of links within their respective bores, it was not possible to be certain that these links always stayed in alignment with one another or properly located within the nut member to receive a pin during subsequent assembly of the inflation device. The finished device manufacturer also realizes a distinct advantage through elimination of the detenting mechanism (i.e., the ribs) because obtaining consistent detent resistance is difficult due to detent interference levels being the product of difficult-to-control tolerance variations from three independent parts that become interdependent when assembled.

A significant additional benefit of providing a unitary link 202 in place of a pair of links is the ability of the unitary link 202 to maintain a more precise longitudinal alignment of the nut member 204 to both the pivot pin 206 and the mating threads 279 on the plunger 238. Precise longitudinal alignment was not previously possible with two separate links since each link was free to pivot out of alignment slightly with the other and consequently allow the nut member to slightly twist or deflect out of alignment with the plunger's axis during engagement and disengagement manipulations. Such twist was possible even though plunger and the pin were maintained in strict parallel alignment to one another. This undesirable deflection offers potential for a deleterious effect upon mating tread components resulting in uneven loading and occasional chipping of the most highly-loaded threads during disengagement during maximum pressure use conditions. A unitary link 202 offers far less potential for twisting or deflection compared to two independent links and thereby yields a more robust mechanism.

Another benefit of the actuating mechanism 246 disclosed herein is the design's self-contained nature, its independence from having to react against any additional external structure to obtain thrust necessary to urge the nut member 204 into constant engagement with the plunger 238. Instead, engagement results from thrust of the unitary link's spring element 276 constantly pulling the nut member 204 toward the pin 206 in order to reach a relaxed unstressed condition. This self-contained action simplifies the overall device design and allows the unitary link 202 to co-exist on the assembly line with the earlier, paired link mechanism in order to allow phasing in of the newer design while the older one remains in production. Medical devices are highly regulated and even minor changes must be properly evaluated and validated by each customer before they can be accepted. Due to need for extensive validation work by each and every customer and changes to printed user instructions, wholesale changeover to a new mechanism is not possible and there will be a period of time where both constructions must be manufactured at the same time as customers switch over, one by one. Not having to change the larger device structure that houses this mechanism reduces overall tooling expense, eliminates processing changes and makes process and component revalidations unnecessary for the device housing 208 structure thereby simplifying and speeding market introduction of the new design.

While an embodiment of the present invention is shown and described, it is envisioned that those skilled in the art may devise various modifications of the present invention without departing from the spirit and scope of the foregoing disclosure.

What is claimed is:

1. A toggle locking mechanism for a fluid displacement device which has a housing and a plunger which extends into the housing, said toggle locking mechanism having a link secured to a locking member, said link configured to provide a biasing force to pull the mechanism into a self-locked condition by drawing the locking member tightly against the link that provides the biasing force.

2. A toggle locking mechanism as recited in claim 1, wherein the locking member comprises a nut member having threads which are biased into engagement with threads on a plunger, but which is selectively disengageable with the threads on the plunger.

3. A toggle locking mechanism as recited in claim 2, wherein the nut member has a lever which is pressable to cause the nut member to disengage the plunger.

4. A toggle locking mechanism as recited in claim 1, wherein a pivot pin secures the link to the locking member.

5. A toggle locking mechanism as recited in claim 4, wherein a rib on the link engages and secures the pivot pin relative to the link.

6. A toggle locking mechanism as recited in claim 1, wherein the locking member comprises a lever and a cam surface, wherein the link has a spring finger which rides up the cam surface of the locking member when the lever of the locking member is pressed.

7. A toggle locking mechanism as recited in claim 6, wherein the cam surface is configured to provide at least one of auditory and tactile feedback regarding whether the locking member is engaged with the plunger.

8. An actuating mechanism on a fluid displacement device which has a housing and a plunger which extends into the housing, said actuating mechanism comprising a nut member which is biased into engagement with the plunger, but which is selectively disengageable with the plunger, wherein the actuating mechanism comprises a unitary link which is on the nut member, wherein the unitary link is secured to the nut member.

9. An actuating mechanism as recited in claim 8, wherein the nut member has a lever which is pressable to cause the nut member to disengage the plunger.

10. An actuating mechanism as recited in claim 8, wherein the nut member comprises threads which engage corresponding threads on the plunger.

11. An actuating mechanism as recited in claim 8, wherein a pivot pin secures the unitary link to the nut member.

12. An actuating mechanism as recited in claim 11, wherein the unitary link has a spring finger which contacts an external surface of the nut member.

13. An actuating mechanism as recited in claim 12, wherein the spring finger is configured to provide that the nut member is biased into engagement with the plunger.

14. An actuating mechanism as recited in claim 12, wherein the spring finger contacts a cam surface on the nut member and provides at least one of auditory and tactile feedback regarding whether the nut member is engaged with the plunger.

15. A method of assembling a fluid displacement device which has a plunger, said method comprising: assembling an actuating mechanism by securing a unitary link to a nut member; securing the actuating mechanism to the fluid displacement device; actuating the actuating mechanism; sticking the plunger through the actuating mechanism; and de-actuating the actuating mechanism, wherein the nut member engages the plunger, wherein the step of assembling the actuating mechanism comprises engaging a unitary link with a nut member, wherein the unitary link tends to stay engaged with the nut member due to a spring finger portion of the unitary link contacting an external surface of the nut member, and using a pivot pin to secure the unitary link to the nut member.

16. A method as recited in claim 15, wherein the step of securing the unitary link to the nut member comprises using a pivot pin to secure the unitary link to the nut member, and having a rib on the unitary link engage and secure the pivot pin relative to the unitary link.

17. A method as recited in claim 15, wherein the step of securing the actuating mechanism to the fluid displacement device comprises using a pin to secure the actuating mechanism.

18. A method as recited in claim 15, wherein the step of actuating the actuating mechanism comprises pressing a lever of a nut member, thereby causing the nut member to traverse relative to the unitary link.

19. A method as recited in claim 18, wherein the step of de-actuating the actuating mechanism comprises releasing the lever of a nut member, thereby causing the nut member to move into engagement with the plunger.

* * * * *